(12) United States Patent
Spector

(10) Patent No.: US 9,020,626 B2
(45) Date of Patent: *Apr. 28, 2015

(54) ORTHOPODS AND EQUIPMENT TO GENERATE ORTHOPEDIC SUPPORTS FROM COMPUTERIZED DATA INPUTS

(71) Applicant: Donald Spector, New York, NY (US)

(72) Inventor: Donald Spector, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/030,081

(22) Filed: Sep. 18, 2013

(65) Prior Publication Data

US 2014/0039657 A1   Feb. 6, 2014

Related U.S. Application Data

(63) Continuation of application No. 11/737,454, filed on Apr. 19, 2007, now Pat. No. 8,583,272, which is a continuation-in-part of application No. 11/408,769, filed on Apr. 21, 2006, now abandoned.

(51) Int. Cl.
| | |
|---|---|
| *G06F 19/00* | (2011.01) |
| *A61F 5/14* | (2006.01) |
| *A43B 7/14* | (2006.01) |
| *G01L 7/00* | (2006.01) |
| *G05B 15/02* | (2006.01) |

(Continued)

(52) U.S. Cl.
CPC ............... *G05B 15/02* (2013.01); *A43B 17/00* (2013.01); *A43D 1/025* (2013.01); *A61B 5/1036* (2013.01); *A61B 5/1038* (2013.01); *A61B 5/6807* (2013.01); *A61B 2562/0247* (2013.01); *A61B 2562/046* (2013.01); *A61F 5/01* (2013.01)

(58) Field of Classification Search
CPC ..................... G05B 19/41865; G05B 19/4099;
A61C 13/0004; B29C 67/0059; B30B 11/005;
A23N 17/005; A43B 7/00; A43B 7/28;
A61B 5/1036; A61B 5/112; A43D 1/025
USPC ................. 700/97, 118, 117; 36/140; 12/142,
12/142 N; 702/139
See application file for complete search history.

(56) References Cited

U.S. PATENT DOCUMENTS 3,791,375 A * 2/1974 Pfeiffer .......................... 600/592
3,974,491 A * 8/1976 Sipe ........................... 340/573.1

(Continued)

FOREIGN PATENT DOCUMENTS

GB    2 300 919 A    11/1996

OTHER PUBLICATIONS

International Preliminary Report on Patentability and Written Opinion of the International Searching Authority of PCT/US07/67052, Apr. 1, 2008.

*Primary Examiner* — Kenneth Lo
*Assistant Examiner* — Jason Lin
(74) *Attorney, Agent, or Firm* — Collard & Roe, P.C.

(57) ABSTRACT

Systems and methods of measuring feet and designing and creating orthopedic inserts are described. The method can include measuring a pressure the foot exerts during a stride at a plurality of points over a period of time, and analyzing a pressure at the plurality of points over the period of time and designing the orthopedic inserter based on the analysis. The system can include a device that measures a pressure exerted by foot at a plurality of times at each of a plurality of points and a computer connected to the device, the computer having a memory that stores the measured pressures and a program operable to analyze the measured pressures to create a design of an orthopedic insert.

11 Claims, 9 Drawing Sheets

(51) Int. Cl.
*A43B 17/00* (2006.01)
*A43D 1/02* (2006.01)
*A61B 5/103* (2006.01)
*A61B 5/00* (2006.01)
*A61F 5/01* (2006.01)

(56) References Cited

U.S. PATENT DOCUMENTS

| | | | | |
|---|---|---|---|---|
| 4,517,696 A * | 5/1985 | Schartz | | 12/1 R |
| 4,647,918 A * | 3/1987 | Goforth | | 340/573.1 |
| 4,734,034 A * | 3/1988 | Maness et al. | | 433/68 |
| 4,745,930 A * | 5/1988 | Confer | | 600/592 |
| 4,813,436 A * | 3/1989 | Au | | 600/592 |
| 4,856,993 A * | 8/1989 | Maness et al. | | 433/68 |
| 4,862,743 A * | 9/1989 | Seitz | | 73/172 |
| 4,876,758 A * | 10/1989 | Rolloff et al. | | 12/142 N |
| 5,033,291 A * | 7/1991 | Podoloff et al. | | 73/172 |
| 5,079,949 A * | 1/1992 | Tamori | | 73/172 |
| 5,088,503 A * | 2/1992 | Seitz | | 600/592 |
| 5,237,520 A * | 8/1993 | White | | 382/154 |
| 5,253,656 A * | 10/1993 | Rincoe et al. | | 600/595 |
| 5,323,650 A * | 6/1994 | Fullen et al. | | 73/172 |
| 5,394,626 A * | 3/1995 | Brown | | 36/99 |
| 5,449,002 A * | 9/1995 | Goldman | | 600/592 |
| 5,449,256 A * | 9/1995 | Sundman | | 409/134 |
| 5,593,699 A * | 1/1997 | Grassi | | 425/2 |
| 5,640,779 A * | 6/1997 | Rolloff et al. | | 33/514.2 |
| 5,678,448 A * | 10/1997 | Fullen et al. | | 73/172 |
| 5,790,256 A * | 8/1998 | Brown et al. | | 356/613 |
| 5,945,610 A | 8/1999 | Galasso | | |
| 6,000,082 A * | 12/1999 | Nguyen | | 12/142 N |
| 6,026,351 A * | 2/2000 | Takeuchi | | 702/155 |
| 6,141,889 A * | 11/2000 | Baum | | 36/140 |
| 6,195,921 B1 * | 3/2001 | Truong | | 36/136 |
| 6,216,545 B1 | 4/2001 | Taylor | | |
| 6,360,597 B1 * | 3/2002 | Hubbard, Jr. | | 73/172 |
| 6,463,351 B1 * | 10/2002 | Clynch | | 700/163 |
| 6,735,547 B1 * | 5/2004 | Yfantis | | 702/155 |
| 6,804,571 B2 * | 10/2004 | Fullen et al. | | 700/118 |
| 7,199,866 B2 * | 4/2007 | Gogolla et al. | | 356/4.01 |
| 7,206,718 B2 * | 4/2007 | Cavanagh et al. | | 702/155 |
| 7,346,418 B2 * | 3/2008 | Lowe | | 700/118 |
| 7,402,148 B2 * | 7/2008 | Brewer | | 602/21 |
| D577,478 S * | 9/2008 | Peveto et al. | | D2/896 |
| 7,617,068 B2 * | 11/2009 | Tadin et al. | | 702/139 |
| 7,661,170 B2 * | 2/2010 | Goode et al. | | 12/1 R |
| 8,036,768 B2 * | 10/2011 | Lowe | | 700/118 |
| 8,117,922 B2 * | 2/2012 | Xia et al. | | 73/862.041 |
| 8,170,705 B2 * | 5/2012 | Koelling et al. | | 700/117 |
| 8,290,739 B2 * | 10/2012 | Tadin et al. | | 702/139 |
| 2001/0047194 A1 * | 11/2001 | Thompson et al. | | 607/59 |
| 2003/0179362 A1 * | 9/2003 | Osawa et al. | | 356/4.09 |
| 2003/0191554 A1 * | 10/2003 | Russell et al. | | 700/187 |
| 2004/0029639 A1 * | 2/2004 | Regan | | 463/42 |
| 2004/0044296 A1 * | 3/2004 | Linton | | 600/595 |
| 2004/0143452 A1 * | 7/2004 | Pattillo et al. | | 705/1 |
| 2004/0168329 A1 * | 9/2004 | Ishimaru | | 33/3 R |
| 2006/0017021 A1 * | 1/2006 | Yoda et al. | | 250/492.23 |
| 2007/0033750 A1 * | 2/2007 | Cook et al. | | 12/134 |
| 2007/0118243 A1 * | 5/2007 | Schroeder et al. | | 700/118 |
| 2007/0250287 A1 * | 10/2007 | Spector | | 702/139 |

* cited by examiner

ORTHOPODS AND EQUIPMENT TO GENERATE ORTHOPEDIC SUPPORTS FROM COMPUTERIZED DATA INPUTS

STATEMENT OF RELATED CASES

This application is a continuation of U.S. patent application Ser. No. 11/737,454, filed on Apr. 19, 2007, which is a continuation-in-part of U.S. patent application Ser. No. 11/408,769, filed Apr. 21, 2006, which is incorporated herein by reference.

BACKGROUND OF THE INVENTION

This product relates to the field of orthopedic inserts for shoes, sneakers and other footwear.

These product lines are typically divided into two categories. One such category is defined by relatively universal insoles that cushion and provide general support. A previous patent discloses the first adjustable insole, in which the bounce of the insole can be controlled by turning a valve. Other products on the market are those such as manufactured under the brand name Dr. Scholl's.

Most of these products tend to be for comfort or support and are universal in use. They are relatively inexpensive.

At the other end of the spectrum are the devices referred to as supports. These are often made by Podiatrists. Podiatrists take imprints and casts of people's feet and then have inserts designed that are made to correct the weight and imprint of the foot.

Accordingly, new and improved methods and systems to provide orthopedic insets are needed.

SUMMARY OF THE INVENTION

One aspect of the present invention is a method of measuring a foot and developing an orthopedic insert. The invention includes measuring a pressure the foot exerts during a stride at a plurality of points over a period of time, analyzing a pressure at the plurality of points over the period of time and designing the orthopedic insert based on the analysis. Another aspect of the present invention also includes milling the orthopedic insert based on the design.

The analysis step can include comparing the pressure at a first of the plurality of points at a first time to the pressure at the first of the plurality of points at a second time. It can also include comparing the pressure at a first of the plurality of points at a first time to the pressure at one or more or plurality of points that are neighbors to the first of the plurality of points.

Another aspect of the present invention provides a device for dynamically measuring pressure exerted by a foot during a stride. The device can include a sock adapted to be pulled over the foot, a plurality of sensors on a bottom surface of the sock, the plurality of sensors adapted to sense pressure exerted by the foot and a communications device on the sock and connected to the plurality of sensors.

The communications device can be a wireless transmitter. It can also include a memory that stores an output of the plurality of sensors. Alternatively, the communications device can include a wired output that can be connected to an external device to download information from the plurality of sensors.

Other devices for dynamically measuring pressure exerted by a foot are also contemplated by the present invention. In accordance with another aspect of the present invention, a device can include a platform long enough to cover at least one stride of the person, a first plurality of pressure sensors along a length of the platform, the first plurality of pressure sensors being wide enough to entirely receive the foot, so that each of the first plurality of pressure sensors can determine a pressure being exerted by the foot at one or more times and an output device connected to the first plurality of sensors.

This device can also include a memory that receives and stores a plurality of pressure measurements from each of the plurality of sensors. This device can also include a second plurality of pressure sensors along a length of the platform, the second plurality of pressure sensors being wide enough to entirely receive the foot, so that each of the second plurality of pressure sensors can determine a pressure being exerted by the foot at one or more times.

The sensors can be piezoelectric devices. They can also be pressure pins.

The platform can also be sized long enough to cover a plurality of strides of the person.

The device can also include imaging means for monitoring the foot during the stride.

Another aspect of the present invention provides a system for measuring a foot and designing and creating an orthopedic insert. The system, in accordance with one aspect of the present invention, includes a device that measures a pressure exerted by a foot at a plurality of times at each of a plurality of points and a computer connected to the device, the computer having memory that stores the measured pressures and a program operable to analyze the measured pressures to create a design of an orthopedic insert.

The system can also include a milling machine that can receive the design of the orthopedic insert and mill the orthopedic insert.

The system can analyze the data in accordance with the methods described herein.

The present invention also contemplates a method and system to make the orthopedic insert with a 3D printer. In accordance with another aspect of the present invention, measurements of a length of two legs are taken as part of the analysis and used with the pressure analysis to create a design of the orthopedic insert. Then the orthopedic insert is made with a 3D printer. The analysis and the making of the orthopedic insert are performed automatically after analyzing the pressure and measuring the length.

DESCRIPTION OF THE EMBODIMENTS

One object of this invention to create a collateral informational base that is immediately capable of altering the manufacture of inserts on a personal basis in an economic way. This can be particularly important since the cost of inserts by podiatrists typically cost hundreds of dollars, for an end product that probably has a cost of goods of only a few dollars. The computerized instructions for the manufacturing of the insert can be transmitted to a foreign country where these inserts can be made by hand or eventually transmitted to machines that can actually create three dimensional moldings that can then be sold to the consumers at a faction of the cost of present inserts sold by Podiatrists. These inserts will also be more accurate since they measure not only static by dynamic motion. This invention involves both the manual and automatic means of manufacturing inserts based on dynamic models from computers.

This system of creating a new type of insole is seen as similar to the revolution that has taken place in optical systems where optometrists have found a way to inexpensively service a great many people with ever more sophisticated forms of glasses and contact lenses at ever decreasing costs.

It is further envisioned that new schools will be set up with a specific syllabi that will teach those that operate such equipment have the necessary information to help customers, but possibly as different degree of training than the traditional podiatrist.

The collateral development of a curriculum and a school for what we will trademark as OrthoPods is also made a part of this instant invention.

Figure 1:
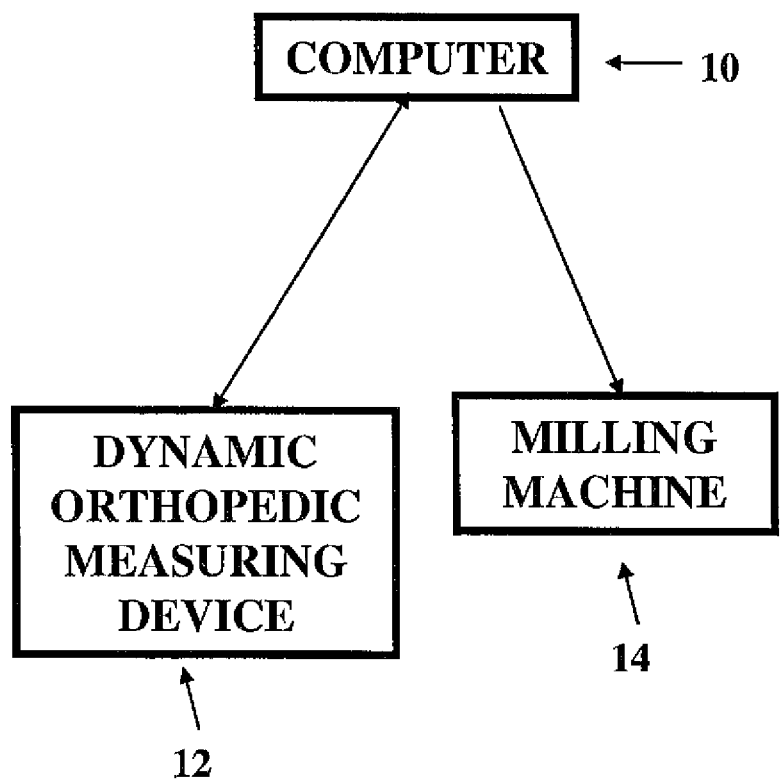
FIG. 1 illustrates a system in accordance with one aspect of the present invention.

FIG. 1 illustrates a system in accordance with one aspect of the present invention. A computer/processor 10 is connected to a dynamic orthopedic measuring device 12. The dynamic orthopedic measuring device 12 measures the pressure from a foot or feet over time, provides the pressure data to the computer 10. The computer analyzes the data and designs an orthopedic insert. The orthopedic insert design is provided by the computer 10 to a milling machine 14. The milling machine 14 creates the orthopedic insert based on the design provided by the computer 10.

Figure 2:
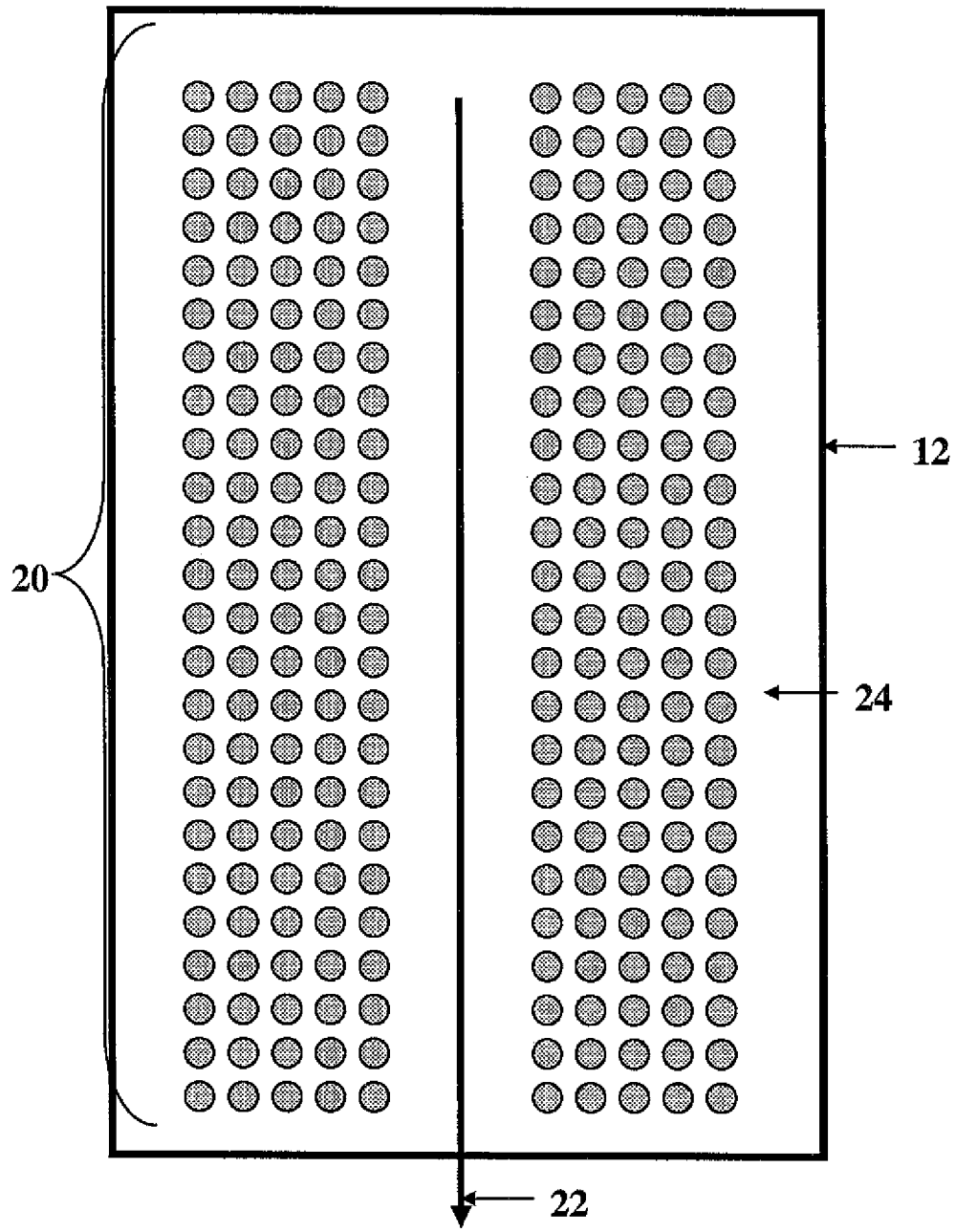
FIGS. 2 and 4 illustrate a dynamic foot measurement device in accordance with a further aspect of the present invention.

FIG. 2 illustrates a dynamic foot pressure measuring device 12 in accordance with one aspect of the present invention. The device 12 includes a platform that is long enough to allow a person to step along device 12, but the device 12 can also be longer to allow multiple strides by a person. The device includes a first plurality of pressure sensors 20. The sensors 20 are wide enough to receive the entirety of a person's foot. A second set of sensors 24 can also be provided so that both feet can be monitored.

The sensors can be piezoelectric devices. The piezoelectric devices sense pressure as a person steps on the device. The sensor can also be pressure pins that sink when a person steps on them. Foot measuring devices that use pressure pins are known.

Each of the sensors senses and records the pressure exerted on it by a foot over time. Thus, the pressure measurement of the foot is dynamic. The pressure sensed can be stored in a memory dedicated to each sensor. Alternatively, the memory can be dedicated to a bank of sensors or the pressure data can be transmitted off the device 12 through the communications link 22 on a real time basis. The communications link is connected, to each of the plurality of sensors. The communications link 22 can be a wireless communication link. Alternatively, it can be a hardwired link that is connected directly to a computer or processor.

Figure 3:
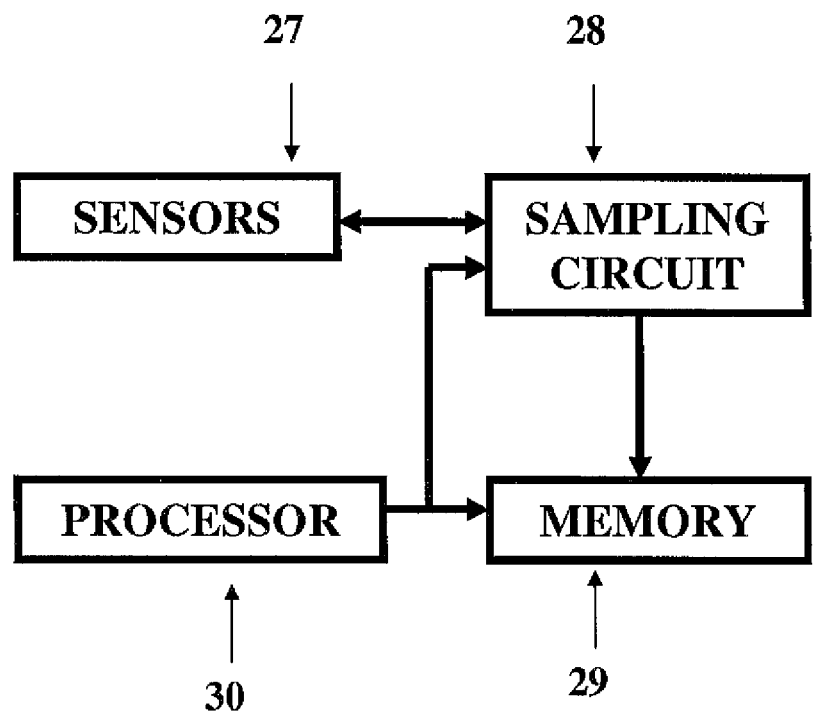
FIG. 3 illustrates a control circuit.

FIG. 3 illustrates a circuit on the device 12. The circuit includes the sensors 27, a sampling circuit 28, memory 29 and, optionally, a processor 30. The sampling circuit 28 controls the frequency of sampling the pressure obtained from each sensor in the sensor banks 27. A sampling frequency in the range of 100 ms to 250 ms is believed to be preferred, however, other sampling frequencies can be used. The sampling frequency can be faster or slower. Thus, each sensor in the bank of sensors 27 will provide a plurality of pressure readings that occur during a person's stride. These readings are stored in the memory 29. The readings stored in the memory 29 can be transmitted to the processor or computer 10 for further analysis. A processor 30 is optionally provided to control the sampling rate used by the sampling circuit 28. Thus, a controller could, depending on the circumstances and results obtained, change the sampling rate.

Figure 4:
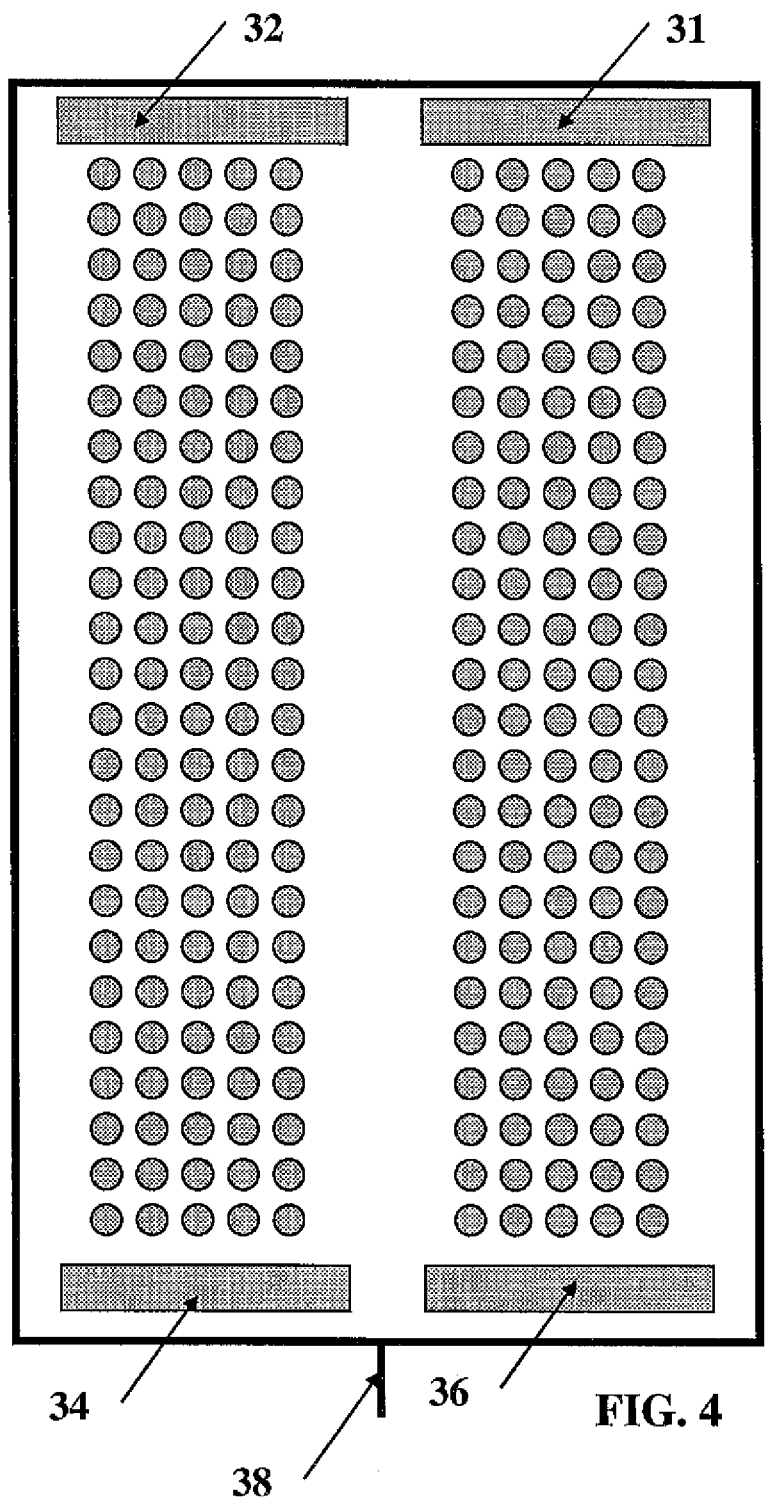

FIG. 4 illustrates another embodiment of the foot measurement device. This device includes the double bank of pressure sensors to measure the pressure exerted by a foot during a person's stride. The device also include four optical devices 31, 32, 34 and 36. These devices monitor the feet during the stride. The devices 31, 32, 34 and 36 can be video cameras, lasers or any other device that creates an image of the feet. These devices 31, 32, 34, and 36 monitor for sideways movement of a foot during a stride. The outputs from the video devices 31, 32, 34 and 36 are connected to the output terminal 38 and fed to a processor. The processor, in accordance with one aspect of the present invention, uses this information to determine any unwanted lateral motion of the foot during a stride.

Figure 5:
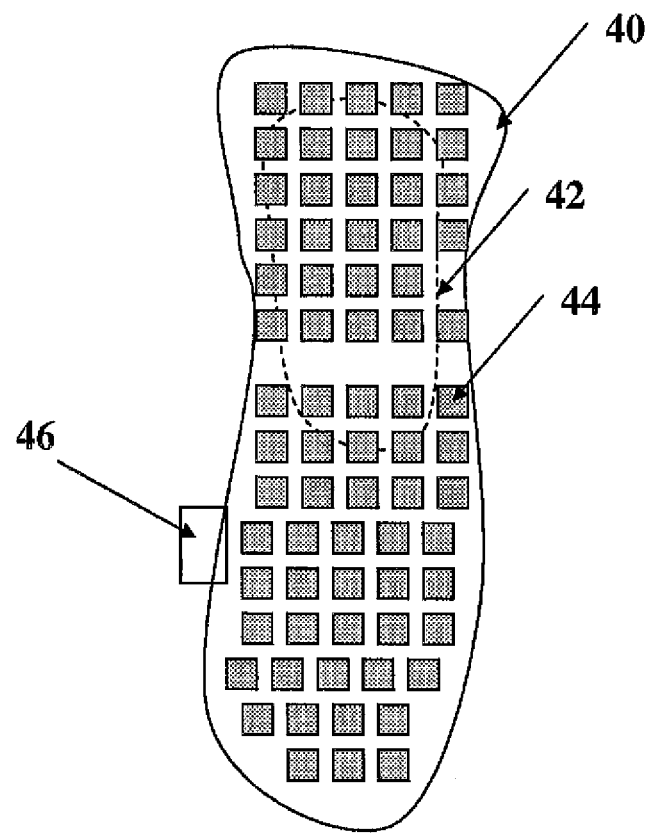
FIG. 5 illustrates another dynamic foot measurement device in accordance with another aspect of the present invention.

FIG. 5 illustrates device for measuring a foot in accordance with another aspect of the present invention. The device 40 is a sock-like device adapted to be pulled over the foot. It can be made of a knitted material that has some stretch to fit over a foot. FIG. 4 illustrates the bottom of the sock 40. The top surface of the sock 40 includes an opening 42 through which the foot fits.

A plurality of sensors 44 are located on a bottom surface of the sock 40. The plurality of sensors 44 are adapted to sense pressure exerted by the foot. The sensors 44 are preferably a piezoelectric devices. A circuit similar to the one illustrated in FIG. 3 is also provided on the sock 40 to control the acquisition of pressure data by the sensors 44.

A communications device 46 is provided on the sock and connected to the plurality of sensors or to a memory containing the data obtained from the sensors 44. The communications device 46 can either be a wireless transmitter or a hard wired communications link. The communications device 46 provides data from the sensors 44 to the processor 10.

Once the data has been provided to the processor 10, the data can be analyzed. It can be analyzed to provide visual depictions of the pressures exerted by a foot at a particular spot or at a number of spots. In accordance with one aspect of the present invention, pressure data obtained from a point over time is analyzed. Additionally, that analysis over time for a plurality of points is also provided.

Figure 6:
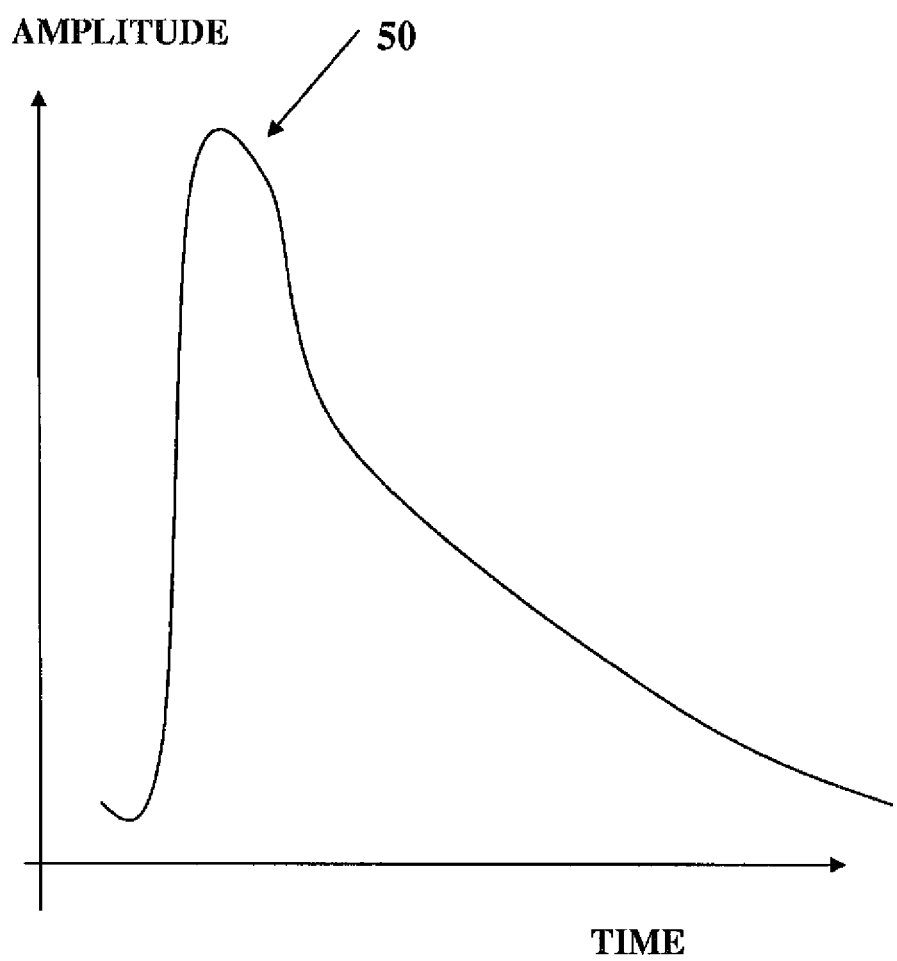
FIG. 6 illustrates a response provided by one of the sensors of a dynamic foot measurement device.

FIG. 6 illustrates a graph of the pressure sensed at one of the sensors over time is illustrated. The point is closer to the heel of the foot. As the heel is planted, the pressure sensed increases at time 50. As the stride continues, the heel lifts up, and the pressure decreases. Graphs of this nature are determined by the processor 10 and available for viewing from the processor 10.

Figure 7:
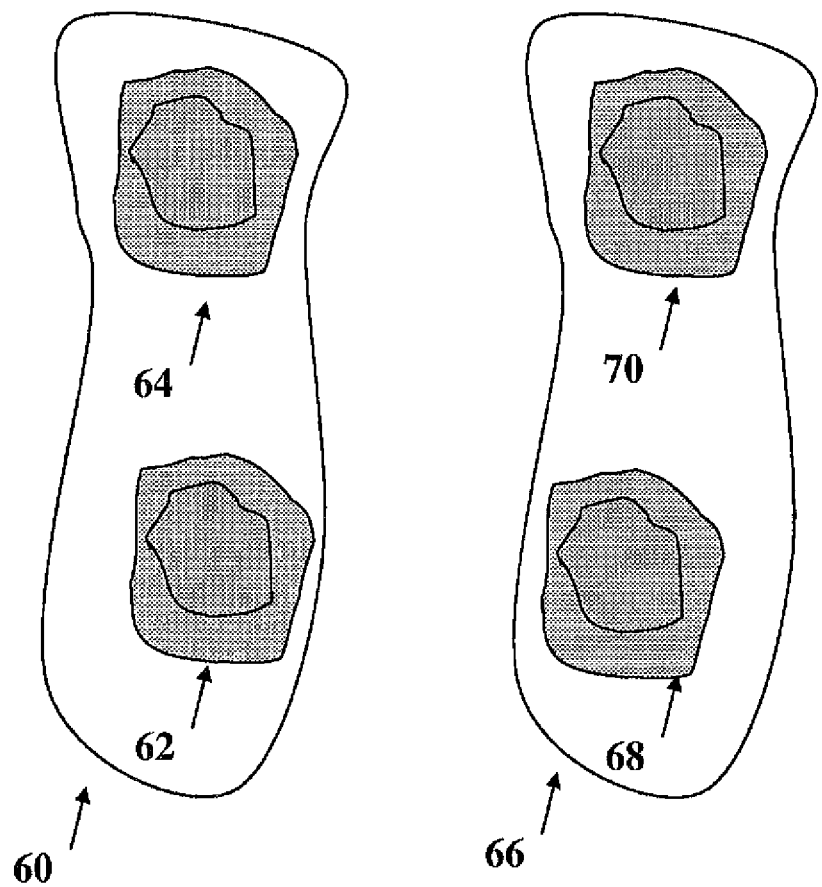
FIG. 7 illustrates computer Images of pressure gradients generated by a dynamic foot measurement device in accordance with one aspect of the present invention.

FIG. 7 illustrates computer images of pressure gradients generated at a first time and at a second time using a dynamic orthopedic insert measuring device. Gradient lines at a first time are illustrated in a first figure 60 at a position 64 near the heel and at a position near the toe 62. Gradient lines at a second time 66 are illustrated in a second FIG. 66 at a position 70 near the heel and at a position near the toe 68.

The graph of FIG. 6 can preferably be obtained in accordance with one aspect of the present invention by clicking on a spot of the gradient display.

In FIG. 7, the inner area at 64 is darker, indicating that there is more pressure being sensed at that point. The outer area at 64 is lighter indicating that there is less pressure being sensed. This is also true at points 62, 68 and 70.

By comparing successive images from successive times, problems with unwanted lateral movement of a foot can be detected. Referring to FIG. 7, for example, in image 60 at a first time, the toe oriented gradients 62 are located closer to the right side of the figure. In image 66, at a second time later than the first time, the pressure gradient has shifted toward the left side of the figure. This is indicative of a rolling problem that can be corrected with an orthopedic insert. The processor 10 detected these problems by comparing the pressure at a first of the plurality of points at a first time to the pressure at the first of the plurality of points at a second time. Each of the points in the array can be compared in this way.

The processor 10 also compares the pressure at a first of the plurality of points at a first time to the pressure at one or more or plurality of points that are neighbors to the first of the plurality of points at a second time. This way the processor 10 detects shifting or side to side pressures that occur during a stride. The processor 10, based on the analysis, designs an orthopedic insert to correct the problem and the milling machine 14 creates the orthopedic insert.

Figure 8:
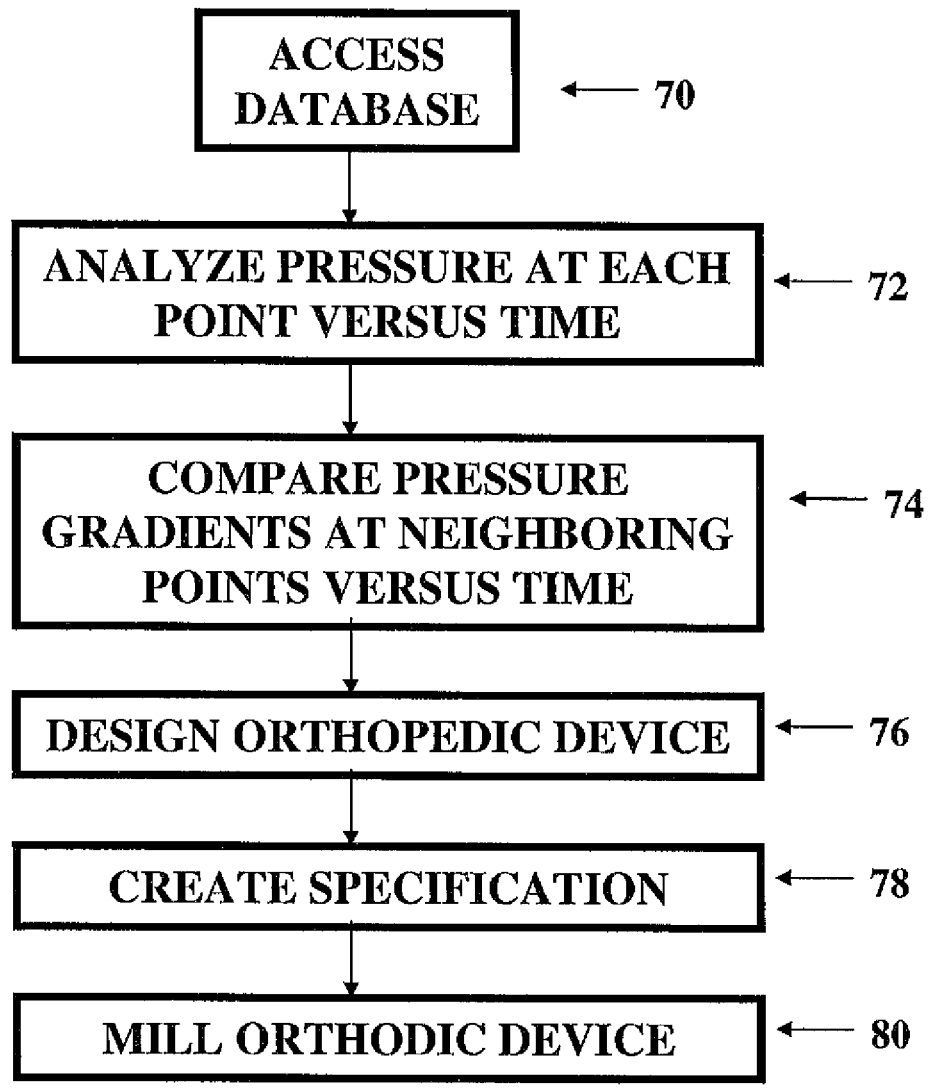
FIG. 8 illustrates a method in accordance with a further aspect of the present invention.

FIG. 8 illustrates a method in accordance with one aspect of the present invention. In step 70, the processor 10 accesses a database. The database stores the pressures sensed at each point in a sensor array at a plurality of times in accordance with the sampling rate. In step 72, the processor analyzes the pressure at each point in time to detect unwanted pressure gradients at any point on the foot. In step 74, the processor analyzes the pressure at neighboring points over time to detect any unwanted shifts of pressure that may occur during a stride. In step 76, based on the analysis, the processor 10 creates an orthopedic insert design. In step 78, a specification is created. In step 80, the milling machine 14 mills the orthopedic insert.

It is believed that almost 90% of the population has two different size legs. Typically, people with two different size legs learn to compensate for this difference by favoring one side. Experts in the field have shown that this is a primary cause of scoliosis, back problems, hip problems as well as pain in later life. This problem can be immediately eliminated using instant 3D foot inserts in accordance with the various aspects of the present invention.

Traditionally, people have gone to podiatrists to make castings, and from these, to make inserts. This process costs several hundred dollars and requires multiple visits. Most people do not go through this effort and expense, unless they have severe problems. However, the chronic problems do not manifest as major problems until later, and are not detected until permanent damages has been done, for example, to the spinal column.

The present invention offers a simple easy technology based on 3D printers that are connected to a computer platform to instantly read and identify problems with weight distribution and the size of a person's leg to automatically print out a plastic insert without the need for casts, multiple visits or large expense.

Figure 9:
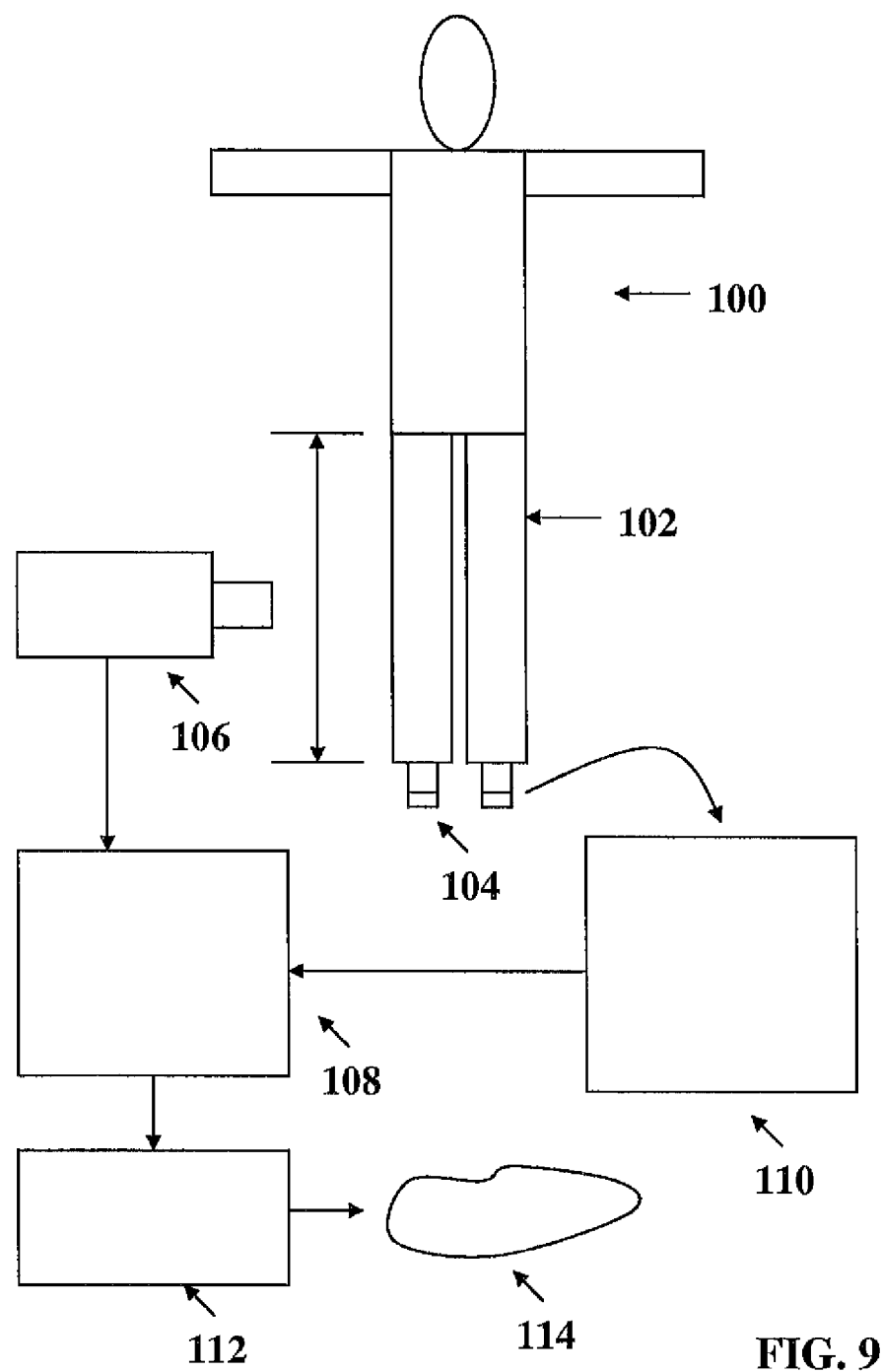
FIG. 9 illustrates a further embodiment of the present invention.

Referring to FIG. 9, a further embodiment of the present invention is illustrated. A person 100 has two legs 102 and two feet 104. The length of the legs 102 is measured and determined using a measuring device 106. The measuring device can be a laser or any other type of measuring device. For example, a simple tape measure could even be used. The length of the legs 102 is entered into a processor 108.

The feet 104 are applied to the pressure measuring device 110, which has been fully described in prior paragraphs. The pressure outputs form the device 110 are transmitted to the processor 108. The processor 108 uses the length of the legs 104, the length of the feet 102 and the pressures exerted by the feet 104 to analyze potential problems and to design an orthopedic insert for each foot 104, as necessary.

The information concerning the orthopedic inserts are transmitted from the processor 108 to a 3D printer 112, also known as a rapid prototyping machine. The 3D printer then instantly generates the necessary orthopedic insert or inserts. 3D printers are available from numerous sources. See, for example, the Z Printer 450 from Z Corporation and the Dimension Elite 3D Printer from Stratasys Corporation. 3D printers are also available from Therice, EOS GmbH, Extrude Hone and Soligen.

It is believed that the service of measuring, analyzing and making orthopedic inserts can be implements in much the same way as one hour glasses. Booths with the necessary equipment to implement the above methodology can be set up at retail outlets or as kiosks at malls. The measurements and analysis from the legs and the feet, either separately or together, are automatically fed into the processor and the inserts are automatically made from the design generated by the processor. The whole procedure can take only minutes and be provided at low cost.

The design is based on known problems and solutions. For example, a low arch can be supported with an insert with a bigger arch. Leg length differences can be compensated for with different size inserts. Many other problems can be corrected using the various aspects of the present invention.

While there have been shown, described and pointed out fundamental novel features of the invention as applied to preferred embodiments thereof, it will be understood that various omissions and substitutions and changes in the form and details of the device illustrated and in its operation may be made by those skilled in the art without departing from the spirit of the invention. It is the intention, therefore, to be limited only as indicated by the scope of the claims appended hereto.

What is claimed is:

1. A method of developing at least one orthopedic insert for footwear used by a person, the method comprising:
   receiving in a computer a data input defining lengths of legs of the person, such input determined by a measuring device;
   receiving in the computer measured values of pressure exerted by each foot of the person during a stride at a plurality of points over a period of time, said measured values being determined by a dynamic pressure sensor;
   receiving in the computer video data that records lateral motion of each foot during a stride;
   analyzing in the computer via a processor the pressure values at the plurality of points over the period of time, the lateral motion, and the leg lengths to produce an analysis;
   designing in the computer with the processor the orthopedic insert based on the analysis;
   transmitting the design of the orthopedic insert from the computer to a 3-dimensional printer; and
   making the orthopedic insert with a the 3-dimensional (3D) printer based on the designing.

2. The method of claim 1, wherein the step of analyzing the pressure values includes comparing the pressure values at a first of the plurality of points at a first time to the pressure values at the first of the plurality of points at a second time.

3. The method of claim 2, wherein the step of analyzing the pressure values includes comparing the pressure values at a first of the plurality of points at a first time to the pressure values at one or more or plurality of points that are neighbors to the first of the plurality of points.

4. The method of claim 1, wherein the step of analyzing the pressure values includes comparing the pressure at a first of the plurality of points at a first time to the pressure values at one or more or plurality of points that are neighbors to the first of the plurality of points.

5. A device for developing at least one orthopedic insert for footwear used by a person, the method comprising:
- a measuring apparatus that determines lengths of legs of the person;
- a platform configured to cover at least one stride of the person;
- a first plurality of piezoelectric pressure sensors along a length of the platform, the first plurality of piezoelectric pressure sensors configured to entirely receive each foot of the person, so that each of the first plurality of piezoelectric pressure sensors can determine values of pressure being exerted by each foot over a period of time at one or more times;
- a video camera configured to record lateral motion of each foot during a stride;
- a processor, coupled to the measuring apparatus, video camera and the sensors, that automatically creates a design of an orthopedic insert based on the pressure values, the leg lengths, and the lateral motion; and
- a 3-dimensional (3D) printer connected to the processor for making the orthopedic insert based on the design.

6. The device of claim 5, wherein the platform is a mat.

7. The device of claim 6, further comprising a kiosk structure that houses the measuring device, the platform, the processor and the 3D printer.

8. The device of claim 5, further comprising imaging means for monitoring each foot during the stride.

9. A system, comprising:
- a first measuring device that determines lengths of legs of a person;
- a second measuring device that measures values of exerted by each foot of the person at a plurality of times at each of a plurality of points during a stride of the person, the second measuring device comprising a sock equipped with piezoelectric sensors that measure pressure exerted by each foot;
- a video camera configured for recording lateral motion of each foot during a stride;
- a computer coupled to the devices and the video camera, the computer having memory that stores the measured pressure values, lateral motion and leg lengths and a program operable to analyze the measured pressure values, lateral motion and the leg lengths to automatically create a design of an orthopedic insert; and
- a 3-dimensional (3D) printer connected to the computer that makes the orthopedic insert based on the design.

10. The system of claim 9, further comprising a kiosk structure that houses the first measuring device, the second measuring device, the computer and the 3D printer.

11. The system of claim 10, wherein the orthopedic insert is made automatically after the device measures the pressure values.

* * * * *